United States Patent [19]

Karger et al.

[11] Patent Number: 5,348,633

[45] Date of Patent: Sep. 20, 1994

[54] METHOD FOR QUANTITATING TRACE AMOUNTS OF AN ANALYTE IN A SAMPLE BY AFFINITY CAPILLARY ELECTROPHORESIS

[75] Inventors: Barry L. Karger, Newton; Kiyohito Shimura, Newtonville, both of Mass.

[73] Assignee: Northeastern University, Boston, Mass.

[21] Appl. No.: 6,922

[22] Filed: Jan. 22, 1993

[51] Int. Cl.⁵ .................... G01N 27/26; G01N 27/447
[52] U.S. Cl. .............................. 204/180.1; 204/182.1; 204/182.8; 204/182.9; 204/183.2; 204/183.3
[58] Field of Search ............ 204/299 R, 182.1, 182.8, 204/183.3, 183.2, 182.9

[56] References Cited

U.S. PATENT DOCUMENTS

| | | | |
|---|---|---|---|
| 4,725,343 | 2/1988 | Hjerten et al. | 204/183.2 |
| 4,911,808 | 3/1990 | Hjerten | 204/182.9 |
| 5,006,210 | 4/1991 | Yueng et al. | 204/180.1 |
| 5,055,415 | 10/1991 | Imai et al. | 204/182.8 X |
| 5,108,568 | 4/1992 | Van Alstine | 204/180.1 |
| 5,120,413 | 6/1992 | Chen et al. | 204/180.1 |
| 5,128,005 | 7/1992 | Jones et al. | 204/180.1 |
| 5,137,609 | 8/1992 | Manian et al. | 204/180.1 |
| 5,149,661 | 9/1992 | Gjerde et al. | 436/178 |
| 5,156,724 | 10/1992 | Jones et al. | 204/180.1 |

OTHER PUBLICATIONS

Chen et al., "Isoelectric Focusing by Free Solution Capillary Electrophoresis," Anal. Biochem. 206:84–90 (1992).
Ernst et al., "Cyanine Dye Labeling Reagents for Sulfhydryl Groups", Cytometry 10:3–10 (1989).
Foret et al., "On–column transient and coupled column isotachophoretic preconcentration of protein samples in capillary zone electrophoresis" J. Chromatogr. 608:3–12 (1992).
Hemmila, *Applications of Fluorescence in Immunoassays*; (Chemical Analysis, vol. 117), J. D. Winefordner, ed.; Wiley–Interscience, New York, pp. 78–80 (1991).
Nielsen et al., "Separation of antibody–antigen complexes by capillary zone electrophoresis, isoelectric focusing and high–performance size–exclusion chromatography", J. Chromatogr. 539:177–185 (1991).
Packard et al., "Site–directed labeling of a monoclonal antibody: Targeting to a disulfide bond", Biochem. 25:3548–3552 (1986).

(List continued on next page.)

*Primary Examiner*—John Niebling
*Assistant Examiner*—John S. Starsiak, Jr.
*Attorney, Agent, or Firm*—Weingarten, Schurgin, Gagnebin & Hayes

[57] ABSTRACT

A method for quantitative detection of trace amounts of an analyte in a sample is disclosed. The method in the preferred embodiment includes providing an Fab' fragment of an immunoglobulin labelled at a reactive sulfhydryl group with a fluorescent dye; combining the labelled Fab' fragment with a sample that may contain the analyte; concentrating the elements of the resulting mixture in an electric field; separating the labelled analyte/agent complex formed from any unreacted labelled agent using capillary electrophoretic methods; and detecting the fluorescent signal of the labelled analyte/agent complex. The invention also is directed to a method of producing a labelled Fab' fragment that includes cleaving an immunoglobulin molecule to obtain one F(ab')₂ fragment; reducing the disulfide-bonds of the F(ab')₂ fragment to obtain two Fab' fragments each having at least one free, reactive sulfhydryl group; and mixing an Fab' fragment having at least one free sulfhydryl group with a fluorescent dye reactive with the free sulfhydryl to form a labelled Fab' fragment. Preferably, prior to the final mixing step, intrastrand disulfide bonds are formed by oxidation within each Fab' fragment, thereby producing individual Fab' fragments each having a single reactive sulfhydryl group. The method of quantitative detection also more broadly includes using any biospecific agent to form a complex with the target analyte.

23 Claims, 9 Drawing Sheets

OTHER PUBLICATIONS

Palmer et al., "*Reduction and Reoxidation of a critical disulfide bond in the rabbint antibody molecule*", J. Biol. Chem. 238:2393–2398 Jul. (1963).

Parham, "*On the Fragmentation of Monoclonal IgG1, IgG2a, IgG2b from BALB/c Mice*", J. Immunol. 131:2895–2902 (1983).

Pikuleva et al., "*Chemical modification of Rabbit IgG with N-dansylaziridine. Investigation of the properties of dansylated antibodies*", Mol. Immunol. 28:311–318 (1991).

Wong, S. "*Chemistry of Protein Conjugation and Cross-Linking*", CRC Press, pp. 248–252, 263 (1991).

Wu et al., "*Capillary Isoelectric Focusing with a universal concentration gradient imaging system using a charge-coupled photodiode array*", Anal. Chem. 64:2934–2941 (Dec. 1992).

Lidofsky et al., "*Laser Fluorescence Immunoassay of Insulin,*" Anal. Chem. 51(11) 1602–1605 (Sep. 1979).

Asja Siseva et al. "Isoelectric Focusing of Insulin, $^{125}$I-Insulin and the $^{125}$I-Insulin-Antibody Complex" Collection Czechoslov. Chem. Commun. vol. 44 (1979) 1828–1834.

METHOD FOR QUANTITATING TRACE AMOUNTS OF AN ANALYTE IN A SAMPLE BY AFFINITY CAPILLARY ELECTROPHORESIS

GOVERNMENT RIGHTS

Part of the work leading to this invention was made with United States Government funds. Therefore, the U.S. Government has certain rights in this invention.

FIELD OF THE INVENTION

The invention relates to methods of quantitatively detecting trace amounts of analytes in samples, and more particularly to formation of labelled complexes of trace analytes and their analysis by capillary electrophoretic techniques.

BACKGROUND OF THE INVENTION

Quantitative analysis of trace amounts of material in a sample ($<10^{-8}-10^{-9}M$) requires sensitive and specific detection methods. Otherwise, identification of trace materials in a sample can be masked by substances found at higher concentrations. Direct measurement of trace materials is often difficult in a small sample due to the low concentration of analyte. This problem is compounded if the substance of interest does not have a physical or chemical property (e.g., UV absorbance) that is easily measurable. Introduction of radioisotopic labels into an analyte can provide a sensitive method of detection; however, disposing of large quantities of radioactive waste can be expensive.

Immunochemical detection using antibodies to a target trace material provides one of the most specific methods to identify trace compounds in a sample. Immunoblotting and ELISA procedures utilize an antibody attached to an enzyme which catalyzes the conversion of an added substrate to a colored or fluorescent product which can be detected. However, crossreactivity and non-specific binding can decrease accuracy, and these procedures can require many steps, expensive chemicals, and long incubation times.

U.S. Pat. No. 5,137,609 to Manian et al. discloses an electrophoresis-based detection system for abundant volumes of target analyte using fluorescently labelled binding agents and measurement of differential migration times. Manian et al. calibrate the apparatus by recording the time when free binding agent arrives at a measuring place, then use this time to establish a window in which to expect the complex. Data from recorded signals from the fluorescent labels are then searched to establish the relationship between free binding agent and bound complex.

Nielsen et al. (J. Chrom. 539:177-185 (1991)) discloses separation of formed antibody/antigen complexes by free solution capillary zone electrophoresis. Direct measurement of UV absorbance of the antigen, antibody or complex is used to detect and identify the complexes.

SUMMARY OF THE INVENTION

The present invention is directed to an analytical method for quantitatively detecting trace amounts ($<10^{-8}-10^{-9}$ M) of analytes in a sample by employing biospecific agents that can form a labelled complex with the analyte and by concentrating and separating the agent/analyte complex from the labelled precursor with rapid, high resolution capillary electrophoretic separation techniques.

In one aspect, the method includes providing as the biospecific agent an Fab' fragment of an immunoglobulin labelled at a reactive sulfhydryl group with a detectable reporter group; combining the labelled Fab' fragment with a sample that may contain the analyte; separating the labelled analyte/agent complex formed from any unreacted labelled agent using capillary electrophoretic methods; and detecting the labelled analyte/agent complex. In preferred embodiments, the Fab' fragment is labelled at a single sulfhydryl group, the reporter group labelling the Fab' fragment is a fluorescent dye for use in laser-induced fluorescence detection, and the elements of the mixture are also concentrated in an electric field.

In a separate aspect of the invention, an Fab' fragment of an immunoglobulin having a reactive sulfhydryl group, for labelling with a reporter group, is produced by cleaving the immunoglobulin molecule with the proteolytic enzyme pepsin to obtain one F(ab')$_2$ fragment, composed of two disulfide-connected Fab units plus the hinge region, and small peptides of the Fc portion. The disulfide-bonded F(ab')$_2$ is then reduced to obtain two Fab' fragments. Preferably, intrastrand disulfide bonds are formed by oxidation, producing individual Fab' fragments each having a single reactive sulfhydryl group.

A labelled Fab' fragment can be prepared by providing an Fab' fragment of an immunoglobulin possessing a reactive sulfhydryl group; providing a detectable reporter group having a site reactive with the reactive sulfhydryl group of the Fab' fragment; and mixing together the Fab' fragment and the detectable reporter group so that the reactive sulfhydryl of the Fab' fragment reacts with the reactive site of the detectable reporter group to form a labelled Fab' fragment.

Figure 1:
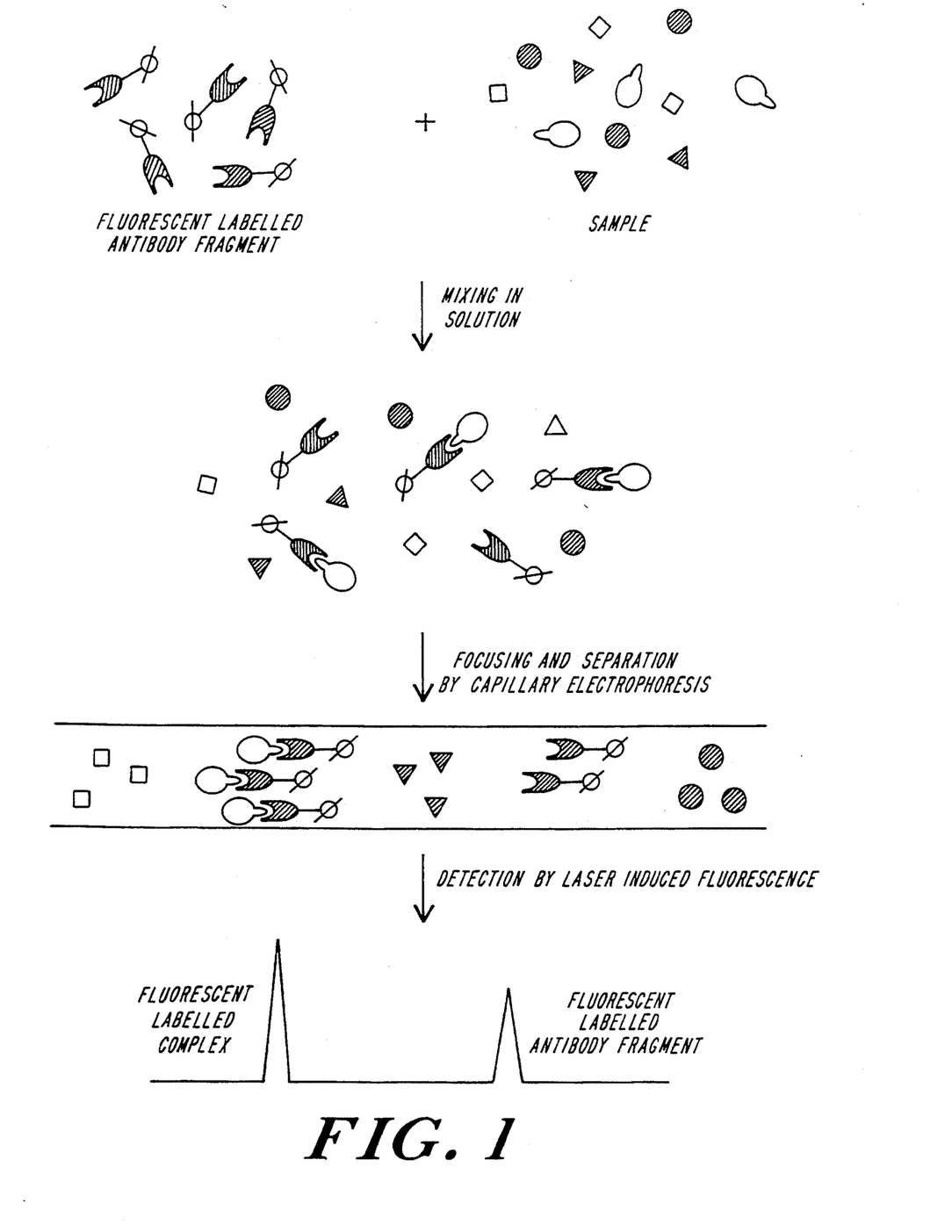
FIG. 1 is a diagrammatic representation of the steps in the method of the invention.

Referring to FIG. 1, the analyte in the sample and the fluorescent labelled antibody fragment, or general biospecific agent, react to form a complex or a "reactive pair" that possesses physical and chemical properties different from those of the labelled agent alone. These properties of the complex allow it to be segregated from the labelled unreacted agent.

The separation method of the invention preferably includes both a concentrating and a separating step. Most preferably, the separating step is carried out in combination with the concentrating step and allows the analyte/agent complex to be concentrated and segregated from the labelled biospecific agent using isoelectric focusing techniques. Alternatively, the concentrating step can be accomplished by (e.g.) isotachophoresis in a microcapillary, followed by separation with capillary zone electrophoresis. Electrophoretic separation may take place in a support medium such as a gel matrix, and running buffers may include additional substances.

In other aspects, the invention more broadly includes other biospecific agents as described in the specification and claims, and the reactive pairs formed with such agents are defined herein to include, but not be limited to, receptor/ligand, binding protein/ligand, single or double stranded oligonucleotides, protein/oligonucleotide, lectin/carbohydrate, and enzyme/inhibitor. Other reporter groups useful in the method of the invention include UV or visible chromophores, radioactive labels, enzymatic reporter groups, ligands, receptors, spin labels, and electrochemical or chemiluminescent labels.

These groups can be detected following complex formation and separation by any appropriate means.

In general, as the method of the invention utilizes capillary electrophoresis for separation of the biospecific agent/analyte complex from free agent or analyte, either of the reactive precursor molecules can be labelled with the reporter group to detect the resulting complex specifically and sensitively. Monoclonal antibodies are more suitable than polyclonal antibodies for this application because of their homogeneity in both binding affinity and electrophoretic mobility. The use of fragments of monoclonal antibody instead of entire molecules avoids the formation of aggregates with antigen. If the biospecific agent is the labelled member of the reactive pair, the sample to be analyzed and the labelled agent are mixed and incubated for an appropriate time to form a agent/analyte complex. If the resulting complex has a different electrophoretic mobility from that of free biospecific agent, the two labelled entities are separated by capillary electrophoresis, and the amount of labelled complex can be detected specifically. In this system, the labelled biospecific agent may be used at relatively high concentration in order to form a reactive pair rapidly, and to obtain a linear response to the amount of analyte to be quantified. This system is appropriate for macromolecular analytes which can effectively change the mobility of labelled biospecific agent on the formation of the complex.

When the analyte is to be the labelled precursor species, the sample to be analyzed is mixed with labelled analyte and non-labelled biospecific agent. After incubation, the labelled complex is separated from labelled analyte by capillary electrophoresis and quantified by fluorescence. As the analyte in the sample will compete with labelled analyte in binding to the agent, the fluorescence signal distribution between the complex and the free labelled analyte should thus be a function of the amount of the analyte in the sample. This system is appropriate for low molecular weight analytes which cannot cause sufficient mobility changes to the biospecific agent on the formation of the immune complex. The mobility of labelled analyte can be controlled with ionic substituents so that it will have a mobility difference sufficient for separation from the complex.

This invention offers the advantages of speed, ease of use, great sensitivity, high resolution of the target analyte, and identification of separated analytes without resorting to additional steps. Target molecules which are in the proper conformation can be distinguished from those which are not. In addition, the small volumes of sample necessary in each assay require the use of only small amounts of expensive reagents, and if an error occurs or the sample precipitates, the capillary column can quickly be washed out and reused.

BRIEF DESCRIPTION OF THE DRAWINGS

Other features and advantages of the invention will be apparent from the following description of the preferred embodiments thereof, taken in conjunction with the accompanying drawings in which.

DESCRIPTION OF THE PREFERRED EMBODIMENTS

Capillary electrophoresis (CE) has recently gained acceptance as a sensitive, fast, and accurate method of analyzing compounds in a mixture, making it particularly important to adapt CE techniques for the performance of trace analysis. Capillary electrophoresis requires only small volumes of sample, and analyses are complete in approximately 20 minutes. The high resolving power of capillary electrophoresis makes it an ideal choice for analysis of complex mixtures, including antigen-antibody complexes.

Generic antibodies or immunoglobulin molecules possess different activities located at different sites on the molecule. Specific antigen binding activity is associated with the variable region of the heavy chain ($V_H$) and the variable region of the light chain ($V_L$) domains located on the Fab fragment, whereas effector functions, such as complement fixation and cell membrane receptor interaction, are usually associated with the Fc fragment. Using a fragment of an immunoglobulin in an immunoassay makes it possible to utilize the activity of one portion of the immunologlobulin without interference from the other domains.

Figure 2:
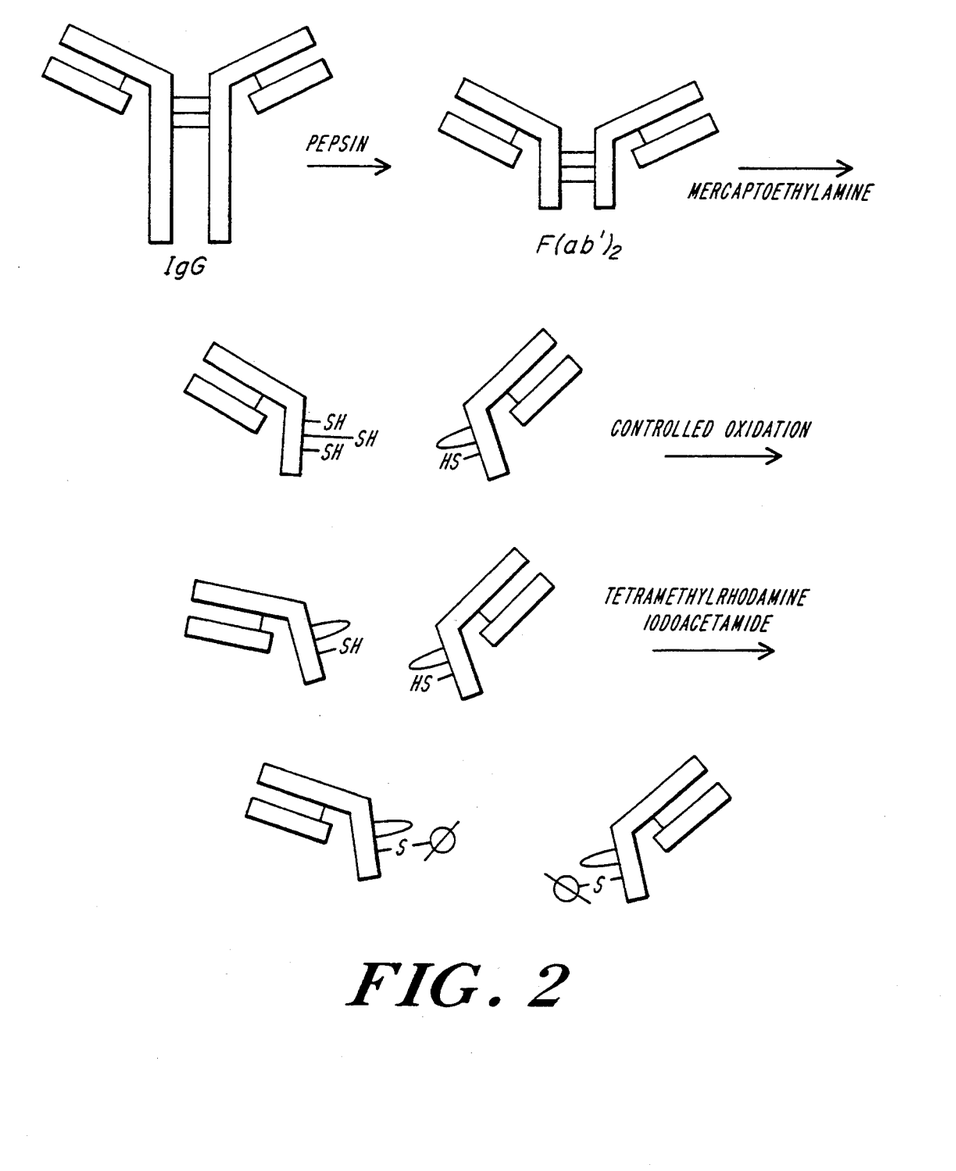
FIG. 2 is a diagrammatic representation of the preparation of a labelled Fab' fragment of mouse IgG1 monoclonal antibody.

An immunoglobulin molecule can be selectively cleaved into fragments, each having discrete activities. Papain cleaves the immunoglobulin molecule into two Fab fragments and one Fc fragment containing the interchain disulfide bonds. By contrast, referring to FIG. 2, cleavage with pepsin produces one F(ab')$_2$ fragment and small peptides of the Fc portion. The resulting F(ab')$_2$ fragment is composed of two disulfide-connected Fab units, plus the hinge region. The disulfide-bonded F(ab')$_2$ fragment may be reduced to obtain two Fab' fragments. After formation of intrastrand disulfide bonds, Fab' fragments each with a single free thiol group are produced.

A single reactive thiol group of a pepsin-generated Fab' unit provides a useful site to attach extrinsic reporter groups or labels, such as fluorophores, chromophores, or binding ligands. The single reactive thiol of the Fab' insures that only one reporter group is attached to each fragment and that the labelling is specific.

If fluorescent reporter groups are used in the invention, certain characteristics are required in order for the method of the invention to be practiced successfully.

Ideally, the attached fluorophore should possess strong absorbance and high fluorescence yield in order to produce a measurable signal during analysis. In addition, the fluorophore should not photobleach significantly during the method of detection and should be pH insensitive in the pH range of operation if isoelectric focusing is employed as the method of separation. Fluorophores that are sensitive to pH are less useful during isoelectric focusing because their quantum efficiency (quantum yield) changes during the migration in the pH gradient. Therefore, an important requirement in the preferred method of the invention is the appropriate choice of a fluorescent label. Preferred fluorescent labelling groups are tetramethylrhodamine iodoacetamide or a cyanine dye.

Furthermore, attachment of the reporter group to the Fab' fragment should be made away from the active site or other areas that participate in the binding reaction to the analyte. It is preferable to attach only one fluorescent reporter group to each Fab' fragment to minimize self-quenching.

An excess amount of appropriately labelled Fab' fragment is then mixed with a sample containing an antigen of interest. The large quantity of labelled antibody fragment shifts the equilibrium of the binding reaction in the direction of complex formation, thus tying up almost all of the antigen. The formed complex is then concentrated and separated from the unreacted Fab' by electrophoretic techniques. Electrophoretic concentration and separation steps take advantage of the unique physical and chemical properties of the antigen-antibody fragment complex. A concentration step allows for more resolute separation of the labelled complex from free antigen and unreacted labelled fragment and for enhanced detection of very small amounts of complex. Preferably, the concentration and separation steps are performed simultaneously by isoelectric focusing.

Isoelectric focusing is an equilibrium process in which all molecules of a given isoelectric point (pI) will migrate to the same region in a medium containing a pH gradient when an electric field is applied. In a preferred embodiment, excess labelled Fab' is reacted with antigen in order to have almost all the antigen molecules reacted with labelled fragment. The unreacted labelled Fab' fragment will have a different pI from that of the reacted complex, and the two species will migrate to different points in the pH gradient.

In an alternative process, concentration and separation can be performed sequentially by isotachophoresis in conjunction with capillary zone electrophoresis, as described in Foret et al., J. Chromatogr. 608:3–12 (1992), hereby incorporated by reference. According to one strategy, on-column transient isotachophoretic migration permits the injection of relatively large volumes of sample into a commercial instrument for subsequent CZE. Alternatively, a coupled column system would permit a higher degree of freedom in the selection of CZE running conditions and the possibility of injection of higher sample volumes.

Antigens that one might identify using the method of the invention include hormones, peptides, enzymes, oligonucleotides, ligands, receptors, carbohydrates, lipids, and haptens. The types of samples that might be analyzed for the presence of the antigen of interest could include serum, plasma, plant extracts, cell extracts, cell culture media, fermentation mixtures, or any complex sample.

The following examples are presented to illustrate the advantages of the present invention and to assist one of ordinary skill in making and using the same. These examples are not intended in any way otherwise to limit the scope of the disclosure.

EXAMPLE I

Figure 3:
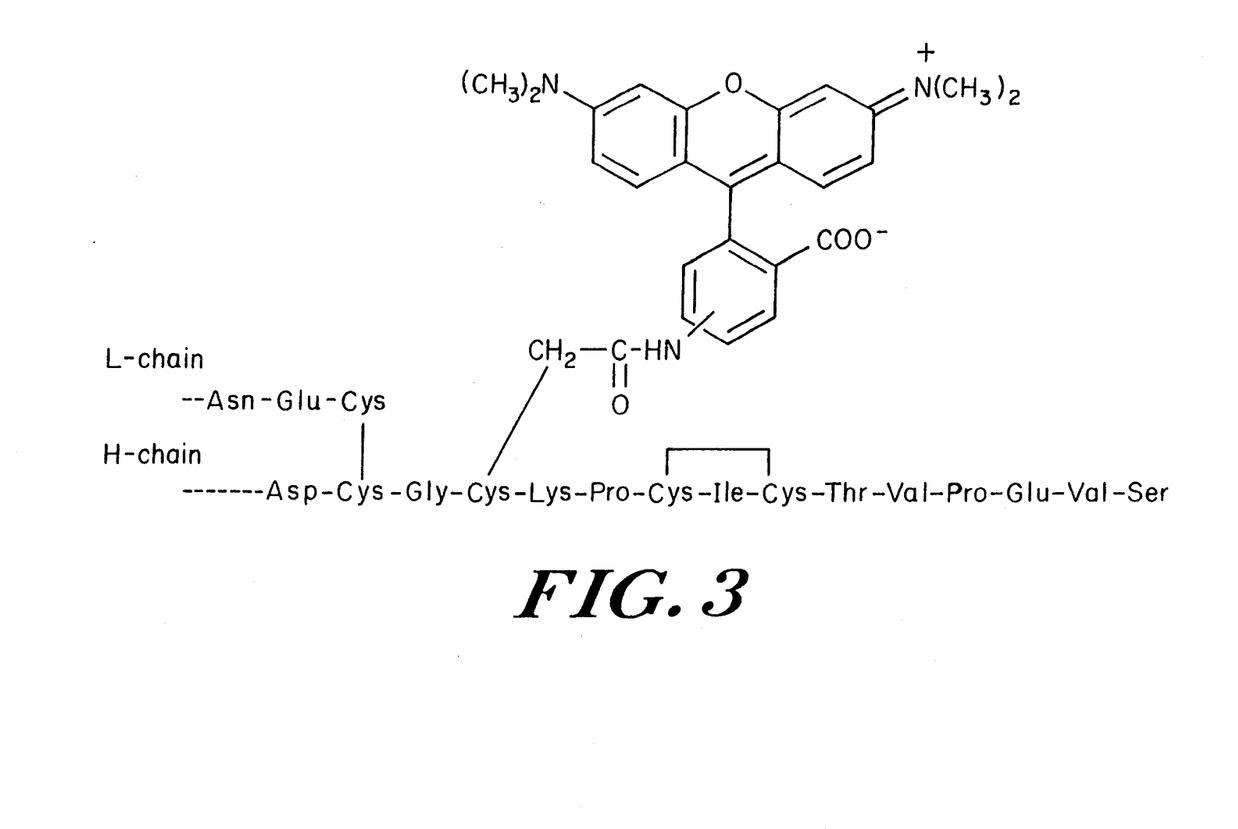
FIG. 3 shows one of the possible structures of the Fab' fragment of IgG1 labelled with tetramethylrhodamine.

In a preferred embodiment, mouse monoclonal IgG1 immunoglobulins (Pierce; Rockford, Ill.) are cleaved with pepsin, and the resulting F(ab')$_2$ fragments are isolated and treated with a reducing agent such as dithiothreitol, dithioerythritol or β-mercaptoethylamine to reduce the three connecting disulfide linkages and produce Fab' fragments. An intrachain disulfide bond between cysteine residues must be formed by oxidation in order to provide only a single reactive thiol group per Fab' molecule. The free sulfhydryl group on each Fab' fragment is labelled with tetramethylrhodamine iodoacetamide (Molecular Probes; Eugene, OR) or cyanine, a fluorescent dye composed of two quaternized heteroaromatic bases joined by a polymethine chain (described in Ernst. et al, Cytometry 10:3–10 (1989), the whole of which is hereby incorporated by reference herein). The fragments are purified before use, e.g., by Imobiline gel electrophoresis (isoelectric focusing) (Pharmacia). One possible structure of a labelled Fab' fragment is shown in FIG. 3, in which an intrachain disulfide bond has been formed between the two cysteine residues separated only by isoleucine while the remaining cysteine residue is reacted through its free sulfhydryl group with the fluorescent dye.

A sample of N-methionyl recombinant human growth hormone (Genentech) is then mixed with an excess amount of labelled Fab' fragment and carrier ampholyte, and the mixture is introduced into a fused silica coated capillary column. Labelled Fab' fragment is supplied in excess so that the reaction with the antigen will be driven to completion in a reasonably short time. The amount of excess labelled Fab' fragment should not be more than 2 to 10 times the amount of expected maximum level of complex. The sample optionally may be treated by dilution or filtering to remove potential contaminants.

The complex formed between the antigen and labelled antibody fragment is separated by isoelectric focusing techniques in which an analyte moves to a position in a pH gradient maintained in the capillary based on its isoelectric point. The silica capillary is coated with polyacrylamide and has a diameter of 5 to 200 μm, with a preferred range being 25 to 100 μm. The sample is mixed with carrier ampholyte and electrically focused for the appropriate time. After focusing, the separated complex is mobilized by the anolyte exchange technique (Hjerten et al., U.S. Pat. No. 4,725,343) and detected by laser induced fluorescence. The use of lasers as excitation sources in fluorometric analyses has led to significant improvements in detection limits of many compounds, e.g., picomole range or less (described in Hemmila, *Applications of Fluorescence in Immunoassays;* (*Chemical Analysis, Vol.* 117), J. D. Winefordner, ed.; Wiley-Interscience, New York (1991), the whole of which is hereby incorporated by reference herein). Alternatively, the separated complex and remaining antibody fragment can be detected in situ by on-line imaging systems, e.g., with laser induced fluorescence.

Figure 4A:
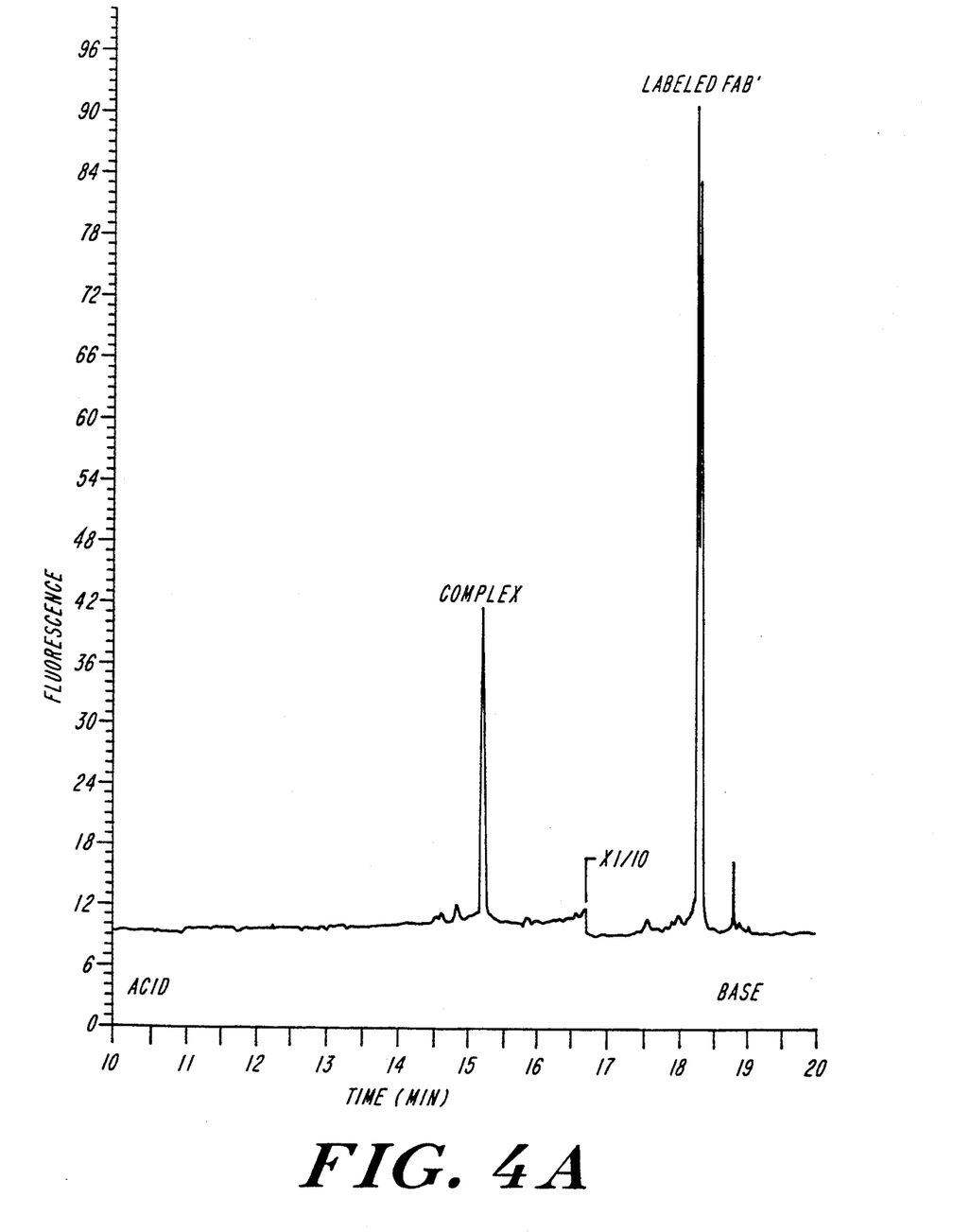
FIG. 4a shows an electropherogram of the complex obtained with tetramethylrhodamine-labelled Fab' and 10 ng/ml N-methionyl human growth hormone.
Figure 4B:
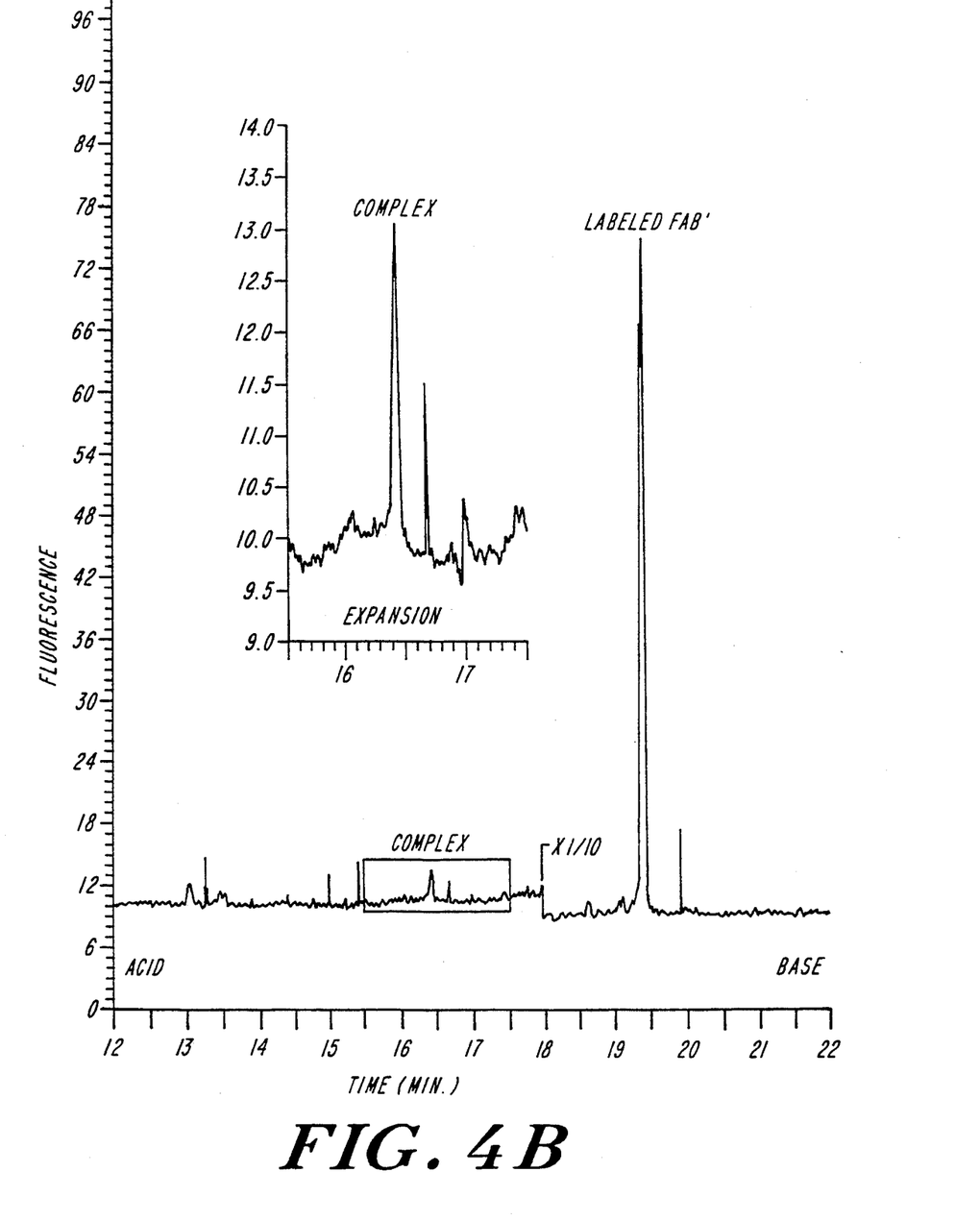
FIG. 4b shows an electropherogram of the complex obtained with tetramethylrhodamine-labelled Fab' and 1 ng/ml N-methionyl human growth hormone.

FIGS. 4a and 4b show the electropherogram obtained with N-methionyl human growth hormone at two different concentrations, 10 ng/ml and 1 ng/ml. Growth hormone solution (4 μl), labelled Fab' fragment solution (4 μl) and 6% Pharmalyte 3-10 (4 μl) were mixed and filled in a capillary (75 μm I.D., 20 cm long, polyacrylamide-coated). Focusing was carried out at 8 kV for 5 min by using 20 mM phosphoric acid as anolyte and 20 mM NaOH as catholyte. A part of the capillary, 8 cm to 18 cm from the anode, was cooled with iced water. Focused bands were mobilized to the anode by changing the anolyte to 20 mMNaOH. Fluorescence (580 was detected at 5 cm from the anodic end with laser excitation (488 nm, 2 mW). Referring to FIG. 4a, an electropherogram of the 10 ng/ml sample shows two major peaks at relatively low sensitivity. The peak at 15.2 min, in the more acidic region, is the complex, and the peak in the more basic region (18.2 min) is the free labelled fragment. At 16.7 min, the sensitivity was decreased 10 times to detect the entire peak of the labelled fragment.

FIG. 4b shows detection of 1 ng/ml of N-methionyl human growth hormones. The complex appeared at 16.4 min, and labelled Fab' appeared at 19.4 min. The inset shows the expansion of the complex peak.

EXAMPLE II

Figure 5:
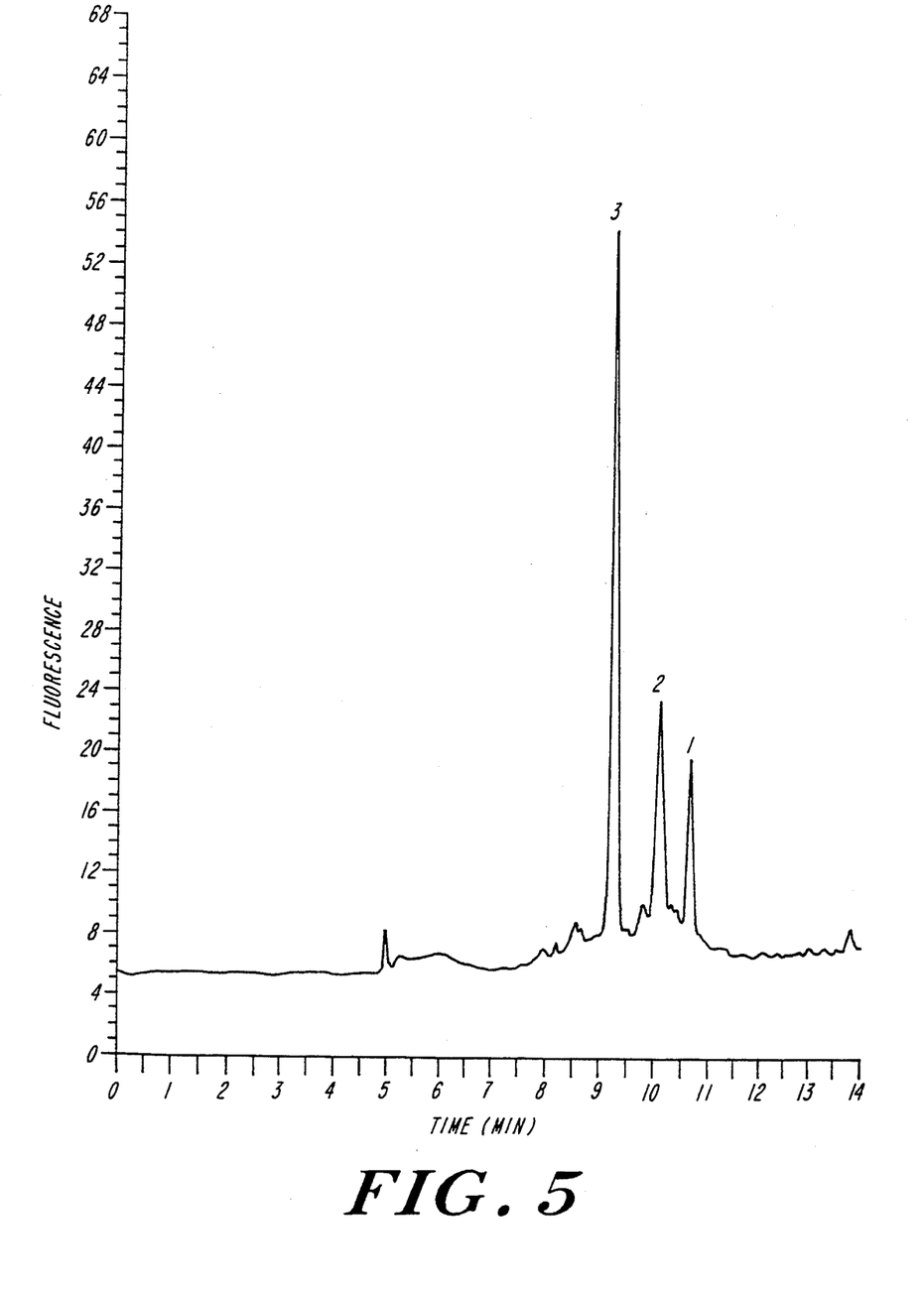
FIG. 5 shows an electropherogram of an artificial mixture containing three human growth hormone variants analyzed with tetramethylrhodamine-labelled Fab'.

Antigen derivatives which differ in isoelectric point may also be analyzed by the method of the invention. For example, an artificial protein mixture containing three human growth hormone species has been prepared. One N-methionyl growth hormone has an additional methionine residue at the N-terminus of human growth hormone. The N149D variant of the N-methionyl growth hormone has a single substitution of asparagine-149 to aspartic acid. Another variant called N149D/N152D is doubly substituted as asparagine 149 and 152 by aspartic acid. To 5 μl of the protein mixture (N-methionyl growth hormone (31 ng/ml); N149D (59 ng/ml); and N149D/N152D (113 ng/ml)) were added 5 μl of tetramethylrhodamine labeled Fab' fragment of antihuman growth hormone monoclonal antibody (700ng/ml) and 5 μl of 6% carrier ampholyte (Pharmalyte 3-10) solution containing 1% polyacrylamide, and the sample was incubated for 5 minutes at room temperature. A polyacrylamide-coated fused silica capillary (75 μm I.D., 15 cm long) was filled with the incubation solution. Isoelectric focusing was carried out at 3kV for 1 minute and 6kV for 4 minutes by using 10 mM phosphoric acid as anolyte and 20 mM NaOH as catholyte. Focused proteins were mobilized toward the anode at 6 kV by changing the anolyte to 10 mM phosphoric acid containing 0.1 M NaCl. Fluorescence (580 nm) was detected at 5 cm from the anodic end with laser excitation (488 nm, 2 mW). The resulting separation of these closely related derivatives is shown in FIG. 5, where peak 1 is N-methionyl-growth hormone; peak 2 is N149D, and peak 3 is N149D/N152D.

EXAMPLE III

Figure 6A:
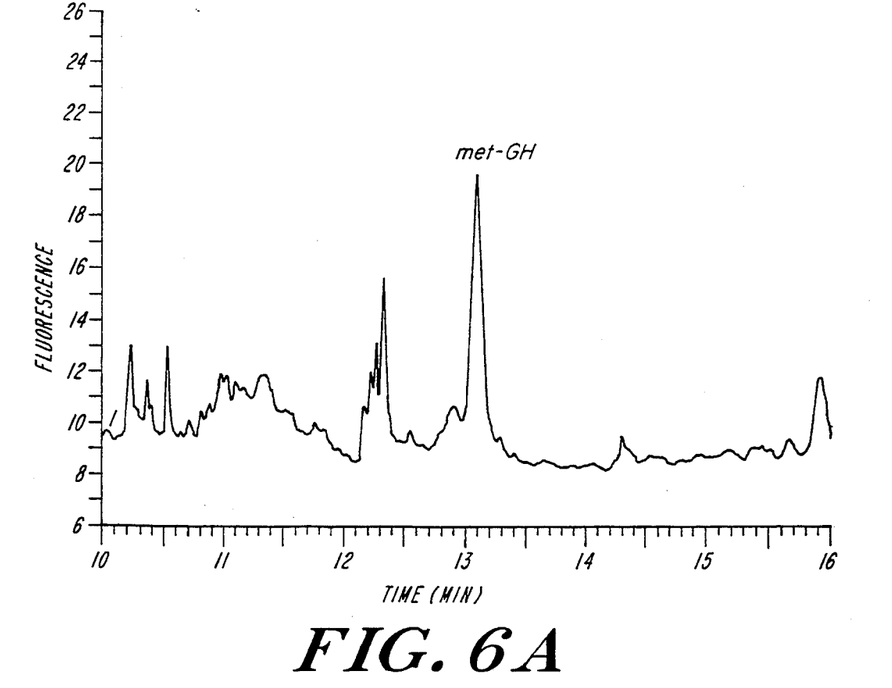
FIG. 6a shows an electropherogram of the complex obtained with tetramethylrhodamine-labelled Fab' and 50 ng/ml N-methionyl human growth hormone detected in 10 times diluted human serum.
Figure 6B:
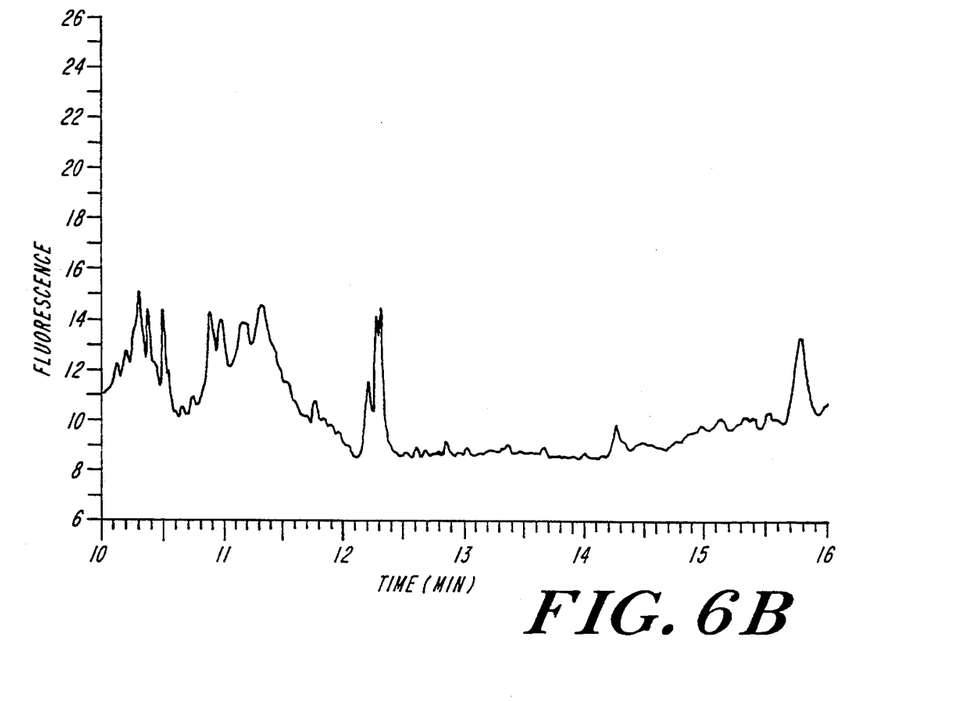
FIG. 6b shows a blank electropherogram with 10 times diluted human serum without N-methionyl growth hormone.

The method of the invention can also be used to detect a specific analyte in a complex mixture. Referring to FIGS. 6a and 6b, an artificial mixture of N-methionyl human growth hormone and human serum was analyzed in the same way as in the experiment described in Example II. FIG. 6a shows methionyl growth hormone (50 ng/ml) in 10 times diluted human serum, and FIG. 6b shows a blank run with 10 times diluted serum without methionyl growth hormone. The peak labeled met-GH in FIG. 6a is clearly detectable against a serum background. Use of the cyanine dyes would reduce the background even further as their absorption maxima are greater than 500 nm. Thus, their detection as reporter groups would be less likely to elicit excitation of serum components.

Use

The special features of direct affinity capillary electrophoresis detection make the method of the invention especially suited for settings in which rapid analysis, high sensitivity, and ease of use are particularly important. For example, a clinical laboratory requires processes that can handle a large number of samples per hour and that can be carried out by technicians without advanced training. Similarly, process stream analysis to support and monitor commercial preparative procedures would benefit from efficient, effective techniques for quantitative analysis as would analyses required to support metabolic studies in pharmacokinetic determinations.

Figure 7:
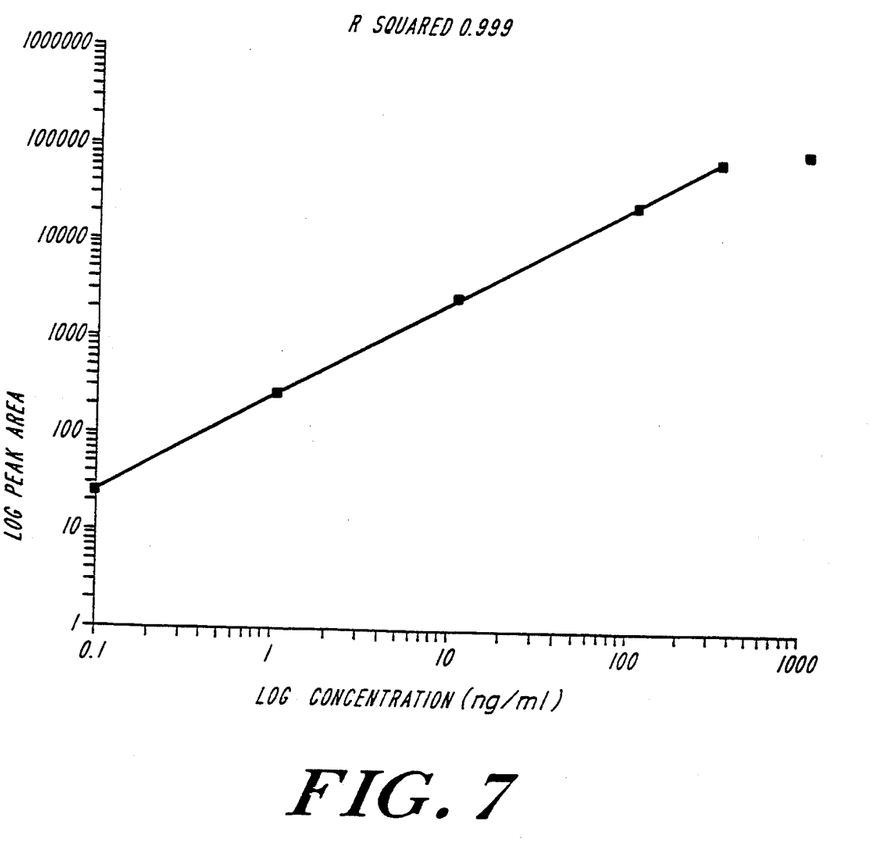
FIG. 7 shows a log-log plot of a standard curve for the quantitative detection of N-methionyl human growth hormone.
Figure 8:
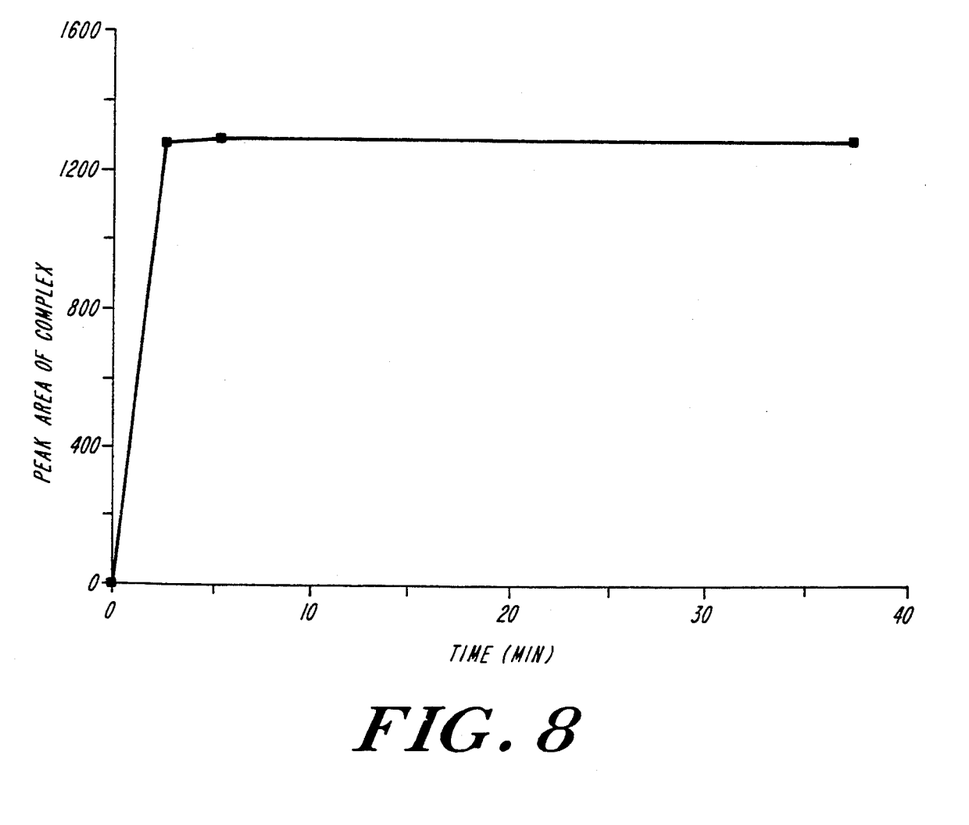
FIG. 8 shows the time course of binding agent/target analyte complex formation.

The quantitative capability and speed that are possible with the method of the invention are illustrated in FIGS. 7 and 8. Referring to FIG. 7, a standard curve on a log-log plot for the quantitative detection of N-methionyl human growth hormone is linear over at least a 1000 fold concentration range, giving a wide range for sample concentration determination. FIG. 8, illustrating the time course of complex formation, shows that the affinity reaction goes to completion in less than five minutes along with the rapid separation, placing the method of the invention well within practical limits for routine use.

For simultaneous handling of multiple samples, a preferred system using fluorescence affinity capillary electrophoresis (FACE) would consist of a battery of microcapillaries laid out in a linear array and capable of simultaneous processing of multiple samples. After separation of the labelled antibody fragment/target analyte complex from unreacted precursor by isoelectrophoresis, the capillaries would be scanned directly for laser induced fluorescence and simultaneously imaged. The sample values would be electronically recorded for real time or subsequent data analysis in the focused state without mobilization. After analysis is completed, the buffer in the capillary columns can be blown out and new runs can be started with little delay. The analysis system easily lends itself to streamlining by automation.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method for quantitatively detecting trace amounts of an analyte in a sample comprising the steps of:
   providing an Fab' fragment of an immunoglobulin labelled at a reactive sulfhydryl group with a detectable reporter group, said labelled Fab' fragment being capable of binding to said analyte to form an analyte-Fab' fragment complex;
   combining said labelled Fab' fragment in a mixture with a sample that may contain said analyte;

separating elements of said mixture by capillary electrophoresis; and detecting said reporter group on said analyte-Fab' complex as an indication of the presence of said analyte in said sample.

2. The method of claim 1, further comprising the step of concentrating elements of said mixture in an electric field.

3. The method of claim 1, wherein said reporter group is selected from the group consisting of fluorophore, UV or visible chromophore, radioisotope, spin label, electrochemical reporter, chemiluminescent reporter, and enzyme.

4. The method of claim 1, wherein said reporter group is a fluorescent dye.

5. The method of claim 1, wherein said reporter group is not sensitive to pH change in the pH range of operation.

6. The method of claim 1, wherein said detectable reporter group is a cyanine or other near infrared excited dye.

7. The method of claim 1, wherein said detection step is by laser induced fluorescence.

8. The method of claim 1, wherein said concentrating step and said separating step are performed simultaneously.

9. The method of claim 1, wherein said concentrating step comprises isotachophoresis.

10. The method of claim 1, wherein said separating step comprises isoelectric focusing.

11. The method of claim 1, wherein said analyte is a peptide or protein.

12. The method of claim 1, wherein said analyte is a derivatized peptide or protein.

13. A method for quantitatively detecting trace amounts of an analyte in a sample comprising the steps of:

mixing together a sample which may contain said analyte and a labelled Fab' fragment that can bind to said analyte to form an analyte-Fab' complex, said Fab' fragment labelled on a reactive sulfhydryl group with a detectable reporter group;

concentrating and separating elements of said mixture by isoelectric focusing; and quantitatively detecting said reporter group on said analyte-Fab' complex as an indication of the amount of said analyte in said sample.

14. The method of claim 13, wherein said detectable reporter group is a fluorescent dye.

15. The method of claim 13, wherein said detectable reporter group is not sensitive to pH change in the pH range of operation.

16. A method for quantitatively detecting trace amounts of an analyte in a sample comprising the steps of:

mixing together a sample which may contain said analyte and a biospecific agent that can bind to said analyte to form an analyte-agent complex, said analyte-agent complex containing a detectable reporter group;

concentrating elements of said mixture in an electric field by a capillary electrophoretic concentration technique;

separating elements of said mixture by a capillary electrophoretic separation technique; and quantitatively detecting said reporter group on said analyte-agent complex as an indication of the amount of said analyte in said sample.

17. The method of claim 18, wherein said biospecific agent is labelled with said detectable reporter group.

18. The method of claim 18 further comprising in said mixing step, mixing a known amount of labelled said analyte, said labelled analyte containing said detectable reporter group.

19. The method of claim 18, wherein said biospecific agent is selected from the group consisting of antibody fragment, binding protein, and ligand.

20. The method of claim 18, wherein said reporter group is selected from the group consisting of fluorophore, UV or visible chromophore, radioisotope, spin label, electrochemical reporter, chemiluminescent reporter, and enzyme.

21. The method of claim 18, wherein said concentrating step and said separating step are performed simultaneously.

22. The method of claim 18, wherein said concentrating step comprises isotachophoresis.

23. The method of claim 28, wherein said separating step comprises isoelectric focusing.

* * * * *

UNITED STATES PATENT AND TRADEMARK OFFICE
CERTIFICATE OF CORRECTION

PATENT NO. : 5,348,633

DATED : September 20, 1994

INVENTOR(S) : Barry L. Karger, et al.

It is certified that error appears in the above-indentified patent and that said Letters Patent is hereby corrected as shown below:

Column 7, line 10, "20 mMNaOH" should read --20 mM NaOH--.

Column 7, line 11, "(580 was" should read --(580 nm) was--.

Column 9, line 25, "claim 1" should read --claim 2--.

Column 9, line 28, "claim 1" should read --claim 2--.

Column 10, line 25, "claim 18" should read --claim 16--.

Column 10, line 27, "claim 18" should read --claim 16--.

Column 10, line 31, "claim 18" should read --claim 16--.

Column 10, line 34, "claim 18" should read --claim 16--.

Column 10, line 39, "claim 18" should read --claim 16--.

Column 10, line 42, "claim 18" should read --claim 16--.

Column 10, line 44, "claim 28" should read --claim 16--.

Signed and Sealed this

Twenty-eight Day of March, 1995

Attest:

BRUCE LEHMAN

*Attesting Officer*   *Commissioner of Patents and Trademarks*